(12) United States Patent
Chauhan et al.

(10) Patent No.: US 7,758,651 B2
(45) Date of Patent: Jul. 20, 2010

(54) MIS PATELLAR PREPARATION

(75) Inventors: Sandeep K. Chauhan, Plumpton Green (GB); Carlos E. Collazo, Old Greenwich, CT (US); Jerry D'Alessio, II, Belleville, NJ (US); Philip F. Williams, III, Teaneck, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 655 days.

(21) Appl. No.: 11/583,469

(22) Filed: Oct. 18, 2006

(65) Prior Publication Data

US 2008/0177394 A1 Jul. 24, 2008

(51) Int. Cl.
*A61F 2/38* (2006.01)

(52) U.S. Cl. ................ 623/20.18; 606/80; 606/86 R

(58) Field of Classification Search .............. 623/20.18, 623/20.19; 606/92
See application file for complete search history.

(56) References Cited

U.S. PATENT DOCUMENTS

| | | | |
|---|---|---|---|
| 3,878,566 A | 4/1975 | Bechtol | |
| 4,041,550 A | 8/1977 | Frazier | |
| 4,158,894 A * | 6/1979 | Worrell | 623/20.18 |
| 4,240,162 A | 12/1980 | Devas et al. | |
| 4,565,192 A | 1/1986 | Shapiro | |
| 4,706,660 A | 11/1987 | Petersen | |
| 4,979,957 A | 12/1990 | Hodorek | |
| 5,021,055 A | 6/1991 | Burkinshaw et al. | |
| 5,129,907 A | 7/1992 | Heldreth et al. | |
| 5,129,908 A | 7/1992 | Petersen | |
| 5,147,365 A | 9/1992 | Whitlock et al. | |
| 5,222,955 A | 6/1993 | Mikhail | |
| 5,246,459 A | 9/1993 | Elias | |
| 5,284,482 A | 2/1994 | Mikhail | |
| 5,342,364 A | 8/1994 | Mikhail | |
| 5,383,937 A | 1/1995 | Mikhail | |
| 5,425,768 A | 6/1995 | Carpenter et al. | |
| 5,437,676 A | 8/1995 | Bouraly et al. | |
| 5,489,310 A | 2/1996 | Mikhail | |
| 5,536,271 A | 7/1996 | Daly et al. | |
| 5,580,353 A | 12/1996 | Mendes et al. | |
| 5,593,450 A | 1/1997 | Scott et al. | |
| 5,662,657 A | 9/1997 | Carn | |

(Continued)

*Primary Examiner*—Bruce E Snow
*Assistant Examiner*—Melissa Montano
(74) *Attorney, Agent, or Firm*—Lerner, David, Littenberg, Krumholz & Mentlik, LLP

(57) ABSTRACT

Instruments and a method for preparing the articular surface of the patella to receive a patellar implant are utilized without everting the patella. A medial or lateral parapatellar incision and an anterior midline incision are made adjacent the patella. The patella is clamped with a patella clamp, a hole is drilled from the anterior surface of the patella. A reamer is inserted through the medial or lateral parapatellar incision and is then attached to the end of a drive shaft that extends outwardly beyond the articular surface of the patella. The posterior facing cutting surface of the reamer device is then placed in contact with the articular surface. The drive shaft is then rotated and moved anteriorly causing the cutting surface of the reamer device to remove a desired amount of patellar cartilage and bone to accommodate a patellar component. The patellar component is secured into place by aligning a central peg protruding from the top surface of the patellar component with the previously drilled hole in the patellar remnant.

18 Claims, 17 Drawing Sheets

U.S. PATENT DOCUMENTS

| | | |
|---|---|---|
| 5,702,467 A | 12/1997 | Gabriel et al. |
| 5,716,360 A | 2/1998 | Baldwin et al. |
| 5,824,099 A | 10/1998 | Mendes et al. |
| 5,871,540 A | 2/1999 | Weissman et al. |
| 6,123,728 A | 9/2000 | Brosnahan et al. |
| 6,190,391 B1 | 2/2001 | Stubbs |
| 6,406,495 B1 | 6/2002 | Schoch et al. |
| 6,494,914 B2 | 12/2002 | Brown et al. |
| 6,506,193 B1 | 1/2003 | Stubbs |
| 6,866,667 B2 | 3/2005 | Wood et al. |
| 2003/0120346 A1 | 6/2003 | Mercinek et al. |
| 2003/0163137 A1 | 8/2003 | Smucker et al. |
| 2004/0162561 A1 | 8/2004 | Marchyn et al. |
| 2005/0177242 A1* | 8/2005 | Lotke ...................... 623/20.19 |
| 2006/0161165 A1* | 7/2006 | Swanson ...................... 606/87 |

* cited by examiner

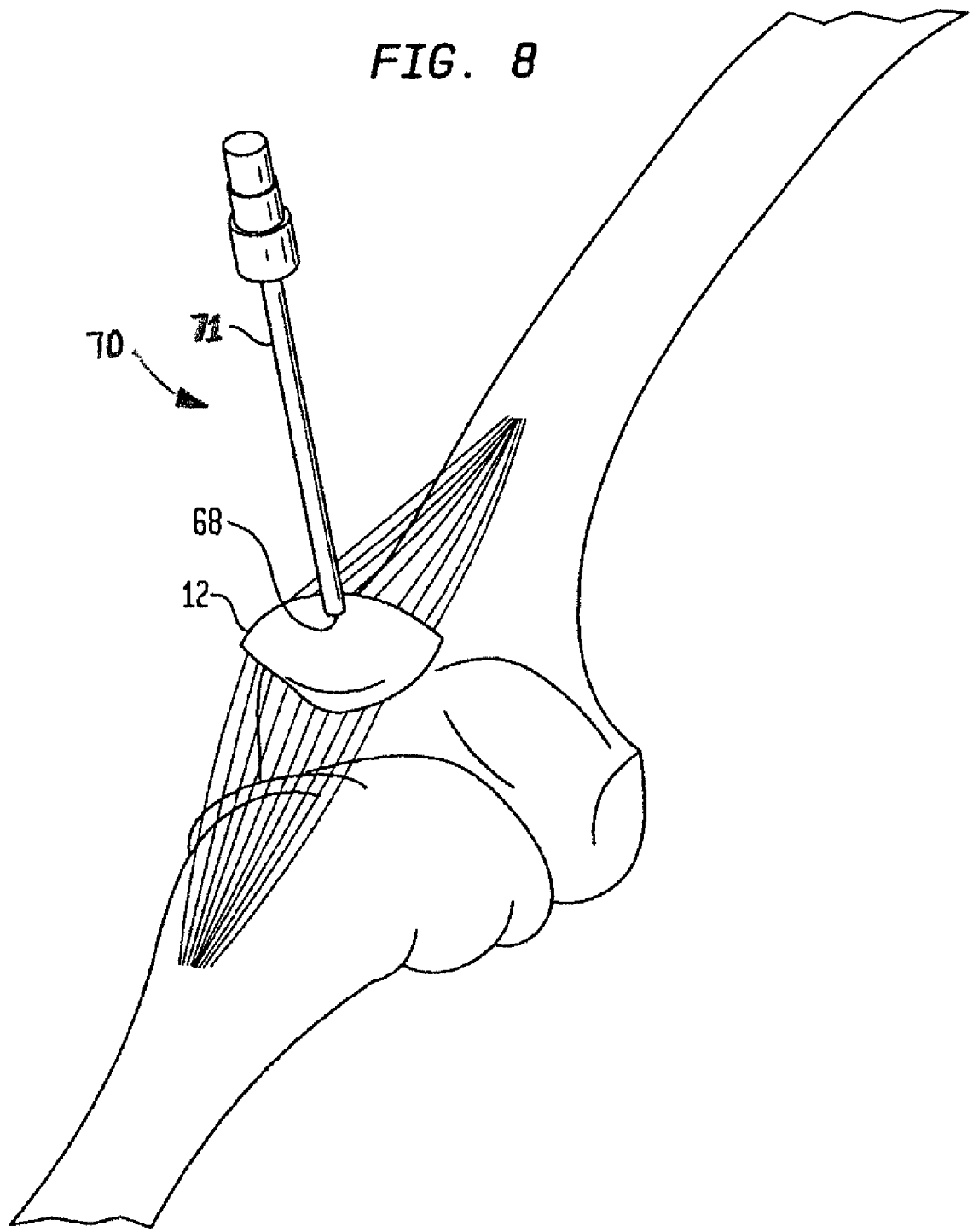

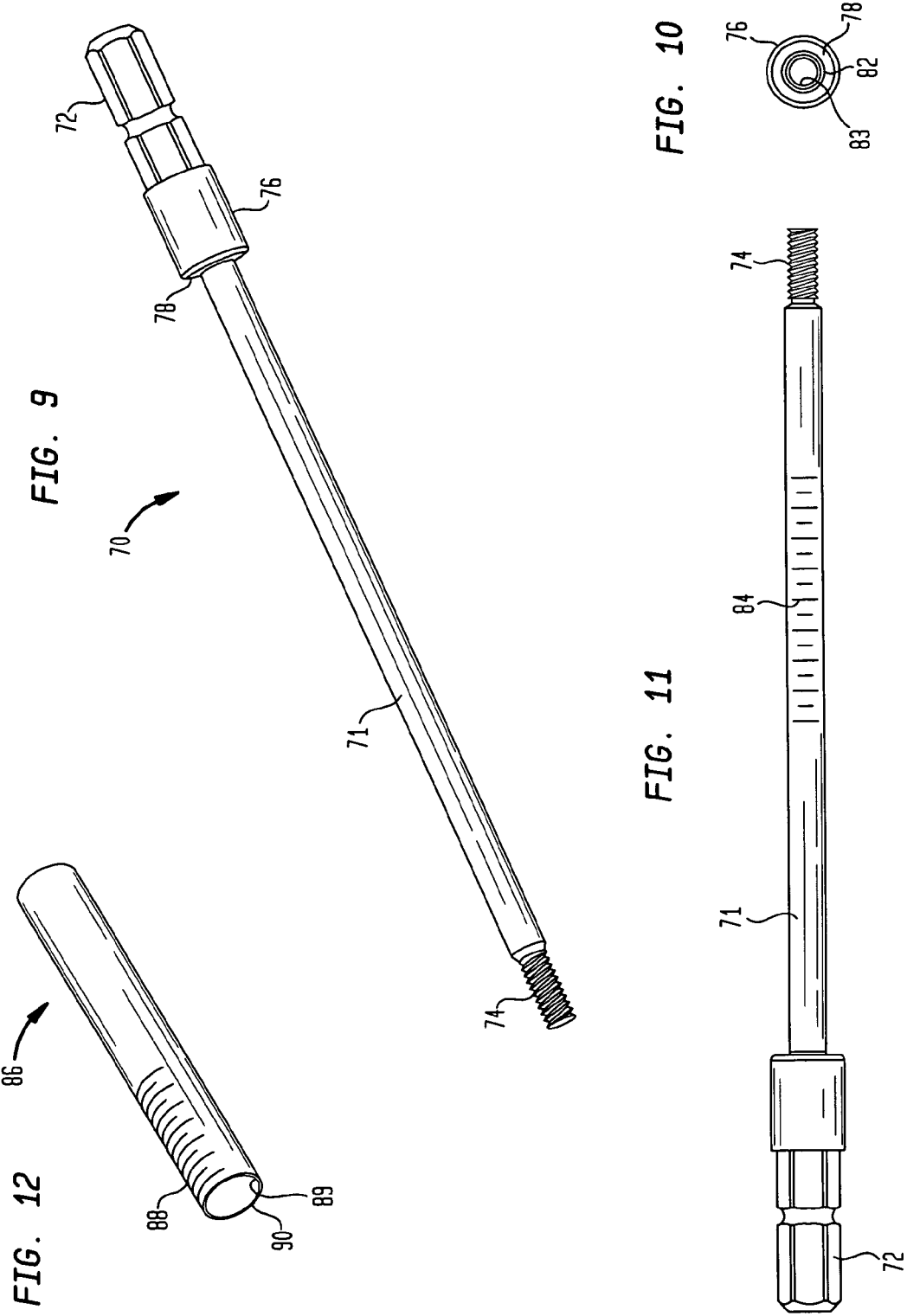

MIS PATELLAR PREPARATION

BACKGROUND OF THE INVENTION

The present invention relates to a minimally invasive apparatus and method for preparing the articular surface of the patella to receive a patellar implant without everting the patella.

Several studies have shown that minimizing the patellar eversion throughout a resection procedure can produce better and faster functional outcomes. Known methods and surgical tools for preparing the articular surface of the patella to receive a patellar component thereon all require eversion of the patella from its anatomically correct position at some point during either resecting the patella for implant fixation, or securing a patella component to the resected patella.

Prior art devices for preparing the patella for receiving a patellar implant are well known to those skilled in the art. It is known in the art to prepare the patella during total knee replacement by everting, i.e. rotating the articular surface anteriorly, the patella approximately 180°, or with newer minimally invasive techniques between 45° and 90°. Patella clamps may be used to clamp the anterior and articular surfaces of the patella before resecting the articular surface of the patella. Additionally, some patella clamps may require fixation pegs or keels to engage the patella before everting it to a desired angle. Common methods to remove bone from the articular surface of the patella include saw resection or milling/planar systems. The removal of bone in either of these systems may provide a flat, stable platform to support, but not secure, a prosthetic patellar component.

For example, Waddell, in U.S. Pat. No. 6,174,314 teaches a patella resection guide and method of resurfacing the patella in situ. In this teaching, after adjustments in a resection guide are made, the patella is cut while in its non-everted position. For non-eversion of the patella to occur during resection, the Peterson device requires a flat or angled saw cut to be made through the resection guide.

U.S. Pat. No. 6,159,246 relates to a surgical method and tool for preparing a patella of the knee joint. Here, a method and device are provided which enable the preparation of a natural patella for accepting a patella implant. The patella is first held with a patella holder or clamp, then everted, and then shaped by means of a bone shaping element.

Other patella resection guides may not evert the patella if a saw is used to cut a desired amount of the articular surface of the patella. Generally when the patella is milled or reamed the patella must be everted at some degree during resection. Further, in order to secure a patella component in any of the prior art systems, at least some eversion of the patella must occur during either resecting the patella or securing a patella component to the resected patella.

Many patella resection guides are known, each having various designs to clamp and mill/saw the patella. Such designs are shown in prior U.S. Pat. Nos. 5,716,360; 5,575,793; 5,536,271; and 5,129,907. Improvements in patella resection guides allowing the patella to be reamed to receive an implant thereon without everting the patella during the reaming step are desirable. A minimally invasive method of preparing the patella to receive an implant thereon without everting the patella is desirable especially where only two small incisions through the skin of the knee are made. Specifically, the articular surface of a patella may be prepared to receive an implant thereon without everting the patella if a medial or lateral parapatellar incision is made through the knee capsule adjacent the patella to gain entry into the knee joint, and another anterior midline incision is made through the skin of the knee down to the anterior surface of the patella bone. More generally, the two incisions may be a medial or lateral parapatellar incision and a small anterior midline incision made above the centerline of the patella. Currently, there is no system that allows the entire patella preparation and implantation of a patellar component to be performed by reaming without everting the patella.

SUMMARY OF THE INVENTION

The apparatus and method of preparing the articular surface of a patella to receive a patellar implant without everting the patella of the present invention addresses and overcomes problems found in the prior art. All of the steps of the present invention may be performed without everting the patella. Specifically, during a reaming step, the reamer device creates a flat, stable platform to mate with a flat top surface of a patella component and also creates a recess in the patella to secure the patella component in place. The recess in the patella is created by a bore forming element protruding from the cutting surface of the reamer device. This recess is provided to house a central peg protruding form the top surface of a patellar component. Therefore, reaming of the patella will also prepare a recess for housing a central peg on the patellar component, allowing for patellar preparation in one reaming step without everting the patella at any time during either resecting the patella or securing a patella component to the resected patella.

The patellar preparation method can be used in patellar replacement (hemiarthroplasty), total knee replacement or patellofemoral replacement. Regardless of the treatment option chosen, two skin incisions may be made in the knee. Specifically, a medial or lateral parapatellar incision and a small anterior midline incision.

A drill bit may be inserted through an anterior midline skin incision, the drill bit advancing through the patella from the anterior surface of the patella and exiting the articular surface of the patella. This hole or pathway can be used to place a drive shaft through the patella bone, the drive shaft extending outwardly from the articular surface of the patella. Further, a reamer or cutter having a receiving end can be placed through the medial or lateral parapatellar incision and then connected to the end of the drive shaft that is extending outwardly from the articular surface of the patella. Preferably, the drive shaft can be assembled to the reamer or cutter in situ. A bore forming element protruding from the cutting surface of the reamer device may be placed in contact with the articular surface of the patella. The drive shaft connected to the reamer device may then be pulled anteriorly to plane the patella flat and create a recess in the patella, the recess later used to receive a central peg of a patellar component therein. Additionally, force may be applied downward on the anterior surface of the patella as the drive shaft is pulled anteriorly so as to create pressure between the articular surface of the patella and the cutting surface of the reamer device. This also allows for there to be less strain on the patella and quadriceps tendon during the reaming step.

In accordance with one aspect of the invention is a method of preparing the articular surface of a patella to receive a patellar component without everting the patella, the method comprising the steps of making a medial or lateral parapatellar incision through the skin of the knee; making an anterior midline incision through the skin of the knee; engaging the articular surface and anterior surface of the patella with a patella clamp; drilling a hole from the anterior surface of the patella to the articular surface of the patella; inserting a drive shaft through the drilled hole of the patella, the drive shaft having a first end that extends outwardly beyond the articular surface; attaching the first end of the drive shaft to a receiving end of a reamer device; placing the reamer device in contact with the articular surface of the patella; resecting the articular surface of the patella by rotating the drive shaft such that the reamer device removes cartilage and bone from the articular surface of the patella; and inserting a patellar component through the medial or lateral parapatellar incision and securing the patellar component to the resected articular surface of the patella.

In accordance with another aspect of the present invention, the method may further include the step of disengaging the patella clamp from the articular and anterior surface of the patella after drilling a hole from the anterior surface of the patella to the articular surface of the patella.

In accordance with another aspect of the present invention, the method may further include the step of centering the reamer device in contact with the articular surface of the patella. The reamer device may further include a bore forming element protruding from the cutting surface of the reamer device that is configured to prepare a recess in the articular surface of the patella as the drive shaft is rotated.

In accordance with another aspect of the present invention, the first clamping part, the second clamping part, and the drill guide each have a central axis.

In accordance with another aspect of the present invention, the method may further include the step of aligning the central axis of each of the first clamping part, the second clamping part, and the drill guide before drilling a hole from the anterior surface of the patella to the articular surface of the patella.

In accordance with another aspect of the present invention, the patellar component includes a central peg which is aligned with the prepared recess of the articular surface of the patella.

In yet another aspect of the present invention is a method of preparing the articular surface of a patella without everting the patella, the method comprising the steps of making a medial parapatellar incision through the skin of the knee; making an anterior midline incision through the skin of the knee; inserting a first clamping part of a patella clamp through the medial parapatellar incision; engaging the articular surface of the patella with the first clamping part; engaging the anterior surface of the patella with a second clamping part of the patella clamp; inserting a drill bit through a drill guide, the drill guide attached to the patellar clamp; drilling a hole from the anterior surface of the patella through the articular surface of the patella; inserting a drive shaft through the drilled hole of the patella, the drive shaft having a first end that extends outwardly beyond the articular surface; inserting a reamer device having a receiving end through the medial parapatellar incision; attaching the first end of the drive shaft to a receiving end of a reamer device; placing the reamer device in contact with the articular surface of the patella; resecting the articular surface of the patella by rotating the drive shaft such that the reamer device removes bone from the articular surface of the patella; and inserting a patellar component through the medial or lateral parapatellar incision and securing the patellar component to the resected articular surface of the patella.

Thus it is an aspect of the present invention to provide an apparatus and method for preparing the patella to receive a patellar component without everting the patella.

It is another aspect of the present invention to resect and prepare the patella to receive an implant thereon without everting the patella during the reaming step.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

BRIEF DESCRIPTION OF THE DRAWINGS

There follows a detailed description of preferred embodiments of the present invention which are to be read together with the drawings therein:

FIG. 8 is an isometric view of a reamer drive shaft inserted into the hole created from the previous drilling operation;

FIG. 9 is an isometric view of the reamer drive shaft of FIG. 8;

FIG. 10 is a bottom view of the drive shaft of FIG. 9;

FIG. 11 is a side view of the drive shaft of FIG. 9;

FIG. 12 is an optimal view of cannula which can receive the drive shaft of FIG. 9;

DETAILED DESCRIPTION

The patellar tendon attaches to the tibial tubercle on the front of the tibia just below the front of the knee. It also is attached to the bottom of the patella. At the top of the patella, the quadriceps tendon is attached. At the top of the quadriceps tendon is the quadriceps muscle. The quadriceps muscle is the large muscle on the front of the thigh. As the quadriceps muscle contracts, it pulls on the quadriceps tendon, the patella, the patellar tendon, and the tibia to move the knee from a flexed position to an extended position. Conversely, when the quadriceps muscle relaxes, it lengthens. This allows the knee to move from a position of extension to a position of flexion.

Figure 1:
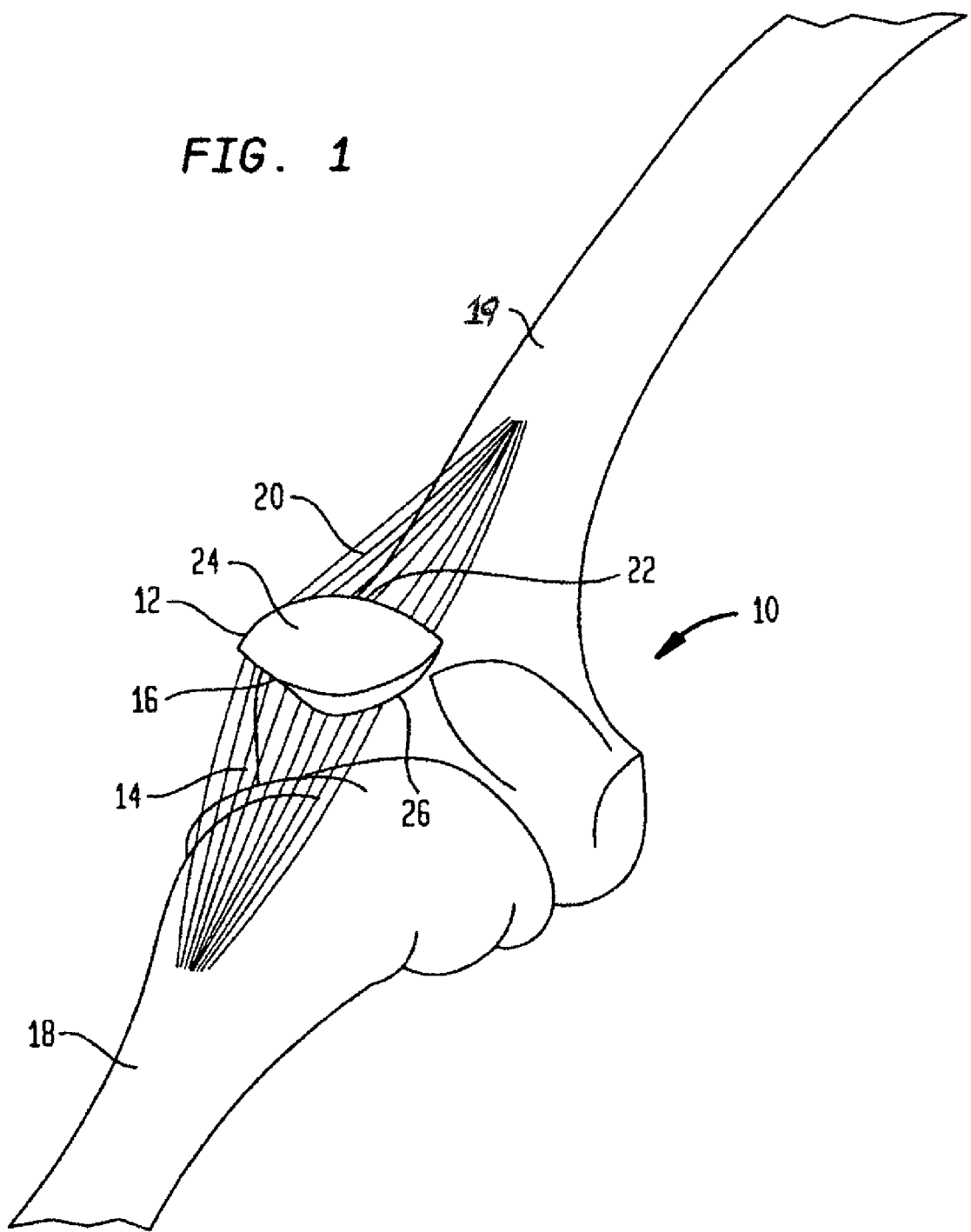
FIG. 1 is an isometric view of a patella connected to the tibia via patellar tendon and connected to the femur via quadriceps tendon.

Referring to FIG. 1, there is shown a knee joint 10 in an extended position with a patella 12 in a non-everted position. Patellar tendon 14 attaches a distal end 16 of the patella 12 to tibia 18. Quadriceps tendon 20 attaches a proximal end 22 of the patella 12 to femur 19. If the patellar tendon 14 ruptures, the patella 12 loses its anchoring support to the tibia 18. Without this anchoring effect of the intact patella tendon 14, the patella tends to move superiorly (towards the hip) as the quadriceps muscle contracts. Without intact patella tendon 14, the patient is unable to straighten the knee 10. If a rupture of patella tendon 14 occurs, and the patient tries to stand up, the knee will usually buckle and give way because the body is no longer able to hold the knee in a position of extension.

In FIG. 1, patella 12 has an anterior surface 24 and a posterior articular surface 26. When the bone of the articular surfaces of femur 19 the knee joint and/or surface 26 of patella 12 is damaged through arthritis or other joint disease or injury or wear, the articular surface 26 may be resected in order to receive a prosthetic patellar component thereon. This is usually done in connection with total knee anthroplasty. If patellar tendon 14 is not ruptured, and the articular surface of the patella is damaged, it is beneficial for a patient receiving a patellar component to have the articular surface prepared to receive a patellar component without everting the patella. In this manner, the patella and quadriceps tendons are not strained if the procedure is performed without everting the patella. This allows for easier recovery after surgery and less post-operative pain.

Figure 2:
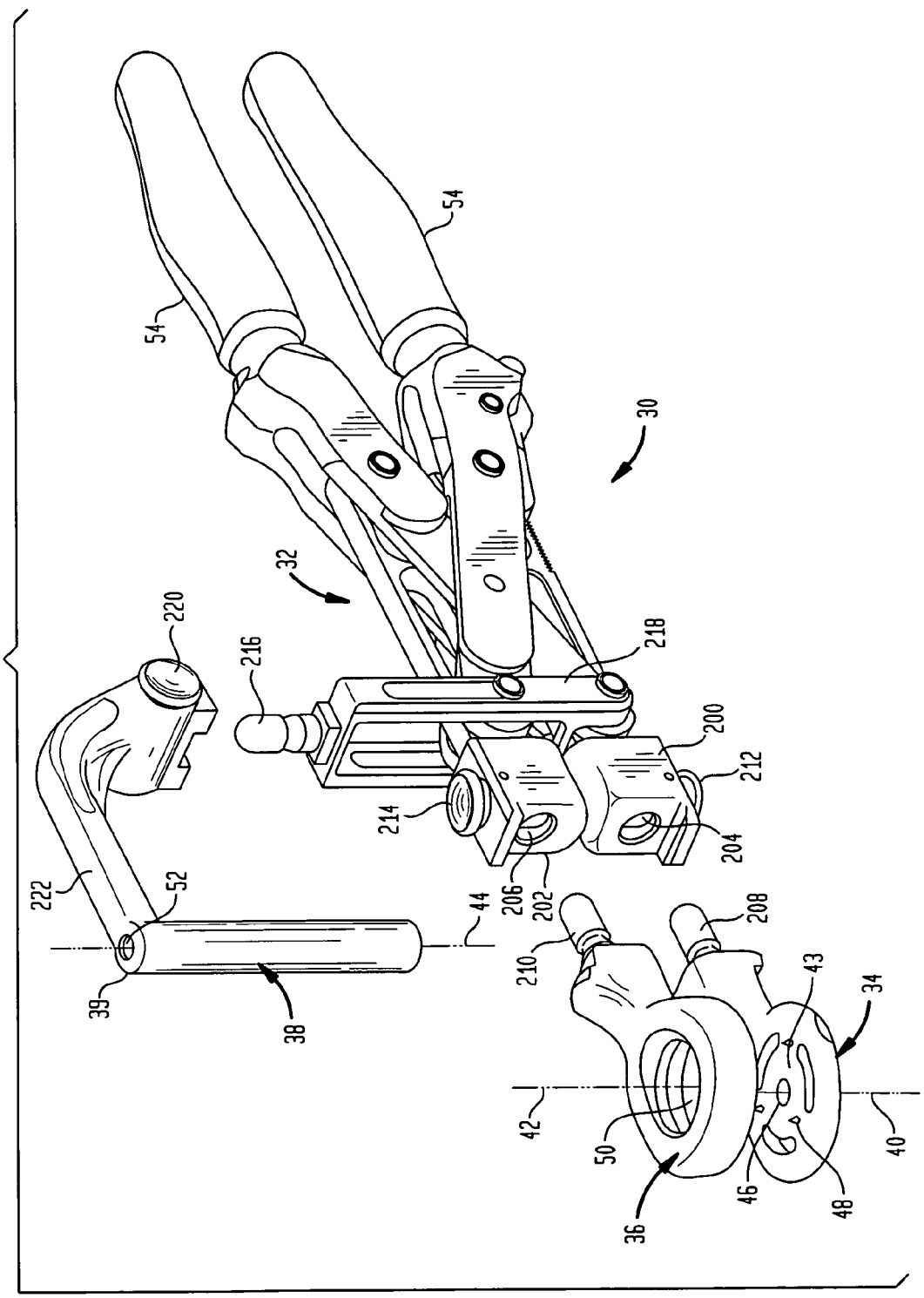
FIG. 2 is an exploded isometric view of a typical embodiment of a patellar clamp for use with the present invention.
Figure 3:
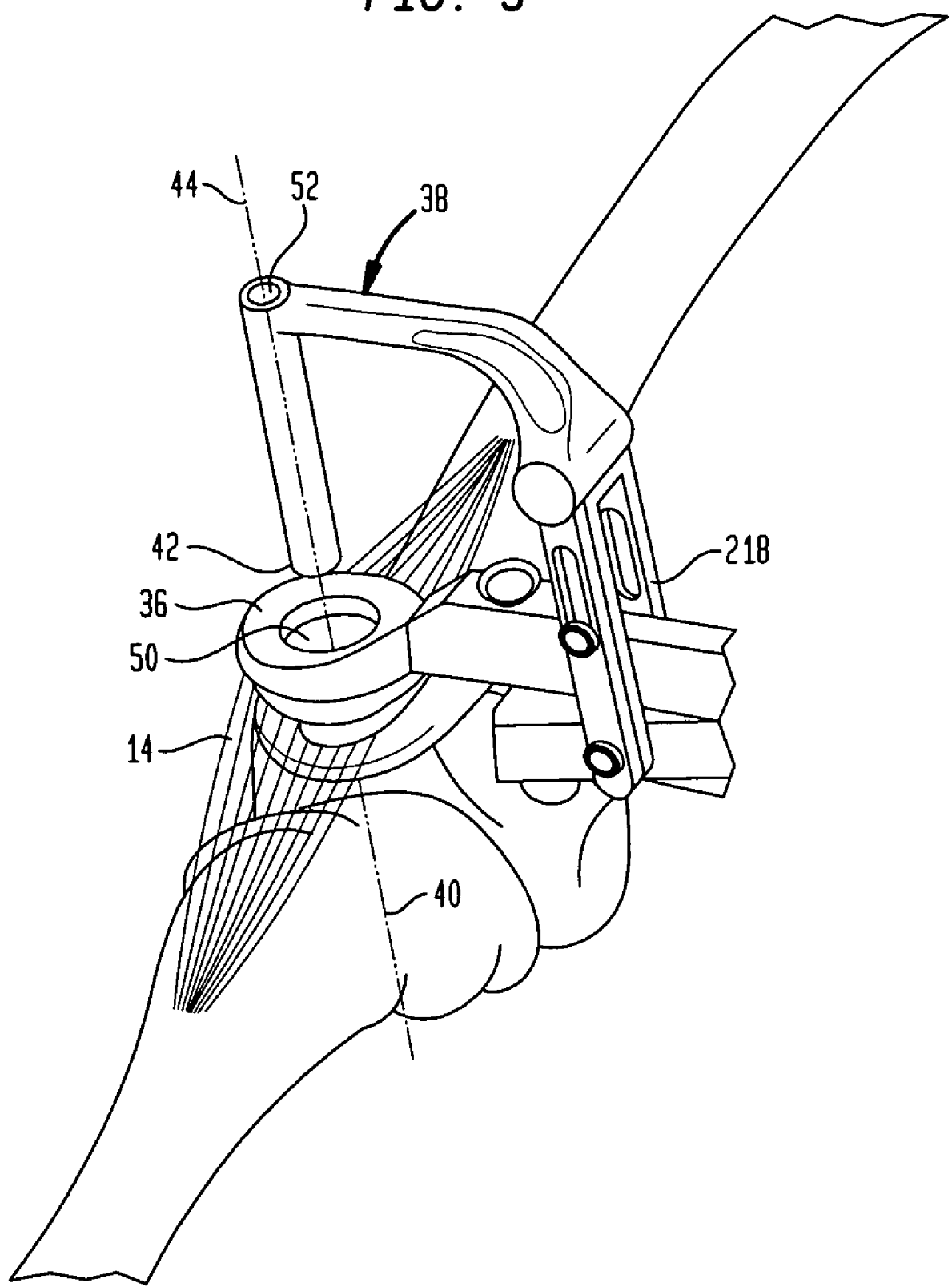
FIG. 3 is a partial assembled isometric view of the patella clamp of FIG. 2 engaging the patella of FIG. 1.

Referring to FIG. 2 there is shown an exploded isometric view of a patellar clamp 30 with a drill guide apparatus 38 for use in the present invention. Such a clamp is shown in U.S. Publication 2004/0162561 the disclosure of which is incorporated herein by reference. Patellar clamp 30 comprises a main body portion 32, a first modular clamping part 34, a second clamping part 36, and a drill guide 38. Main body portion 32 of patellar clamp 30 includes a pair of handle portions 54 which are connected to moveable receptacles 200 and 202 which are coupled to the handle 54 by a linkage mechanism such as described in U.S. Publication 2004/0162561. Receptacles 200 and 202 include bores 204 and 206 into which insertion portions 208 of clamping part 34 and 210 of clamping part 36 are inserted. Insertion portions 208 and 210 are held within receptacles 202 and 204 by spring detent which can be released by depressing buttons 212 and 214. Likewise an insertion element 216 is mounted on a frame 218 which is coupled to the linkage mechanism of main body portion 32. Drill guide 38 may be releasably attached to insertion portion 216 and, although not shown in FIG. 2, includes a receptacle similar to 202 and 204 with a quick release button 220 which operates in a similar manner as release buttons 212 and 214. Drill guide 38 includes a support arm 222 which allows the drill guide barrel 39 of drill guide 38 to be placed adjacent the centers of first and second clamping parts 34, 36. Barrel 39 includes an opening 52 through which a drive element or drill bit (not shown) may be inserted along axis 44. When clamping parts 34, 36 of patellar clamp 30 are assembled as shown in FIG. 3, a central axis 40 of first clamping part 34 and a central axis 42, of second clamping part 36, and a central axis 44 of drill guide 38 are aligned. First clamping part 34 includes a bore 46 to allow a drill bit inserted through an opening 52 of drill guide 38 to extend outwardly beyond articular surface 26 of patella 12, and thus will protect the anterior aspect of a native femur.

Additionally, the preferred surgical method of the present invention is a minimally invasive procedure for preparing the articular surface of the patella to receive a patellar implant without everting the patella. Before the apparatus of the present invention is inserted into the body, two skin incisions are preferably made through the skin of the knee. Specifically, a medial or lateral parapatellar incision and a small anterior midline incision are made. Once exposure to the knee is attained, the clamping part of a standard patellar clamp is inserted into the joint of the knee. For example with the knee in full extension, a first clamping part 34 of patella clamp 30 is inserted through the medial or lateral parapatellar incision. Preferably, patella 12 may be slightly raised in the anterior direction without everting the patella, to accommodate first clamping part 34 of patella clamp 30 thereunder. The top surface 43 of first clamping part 34 is brought into contact with articular surface 26 of patella 12. The articular surface 26 of patella 12 should be centered along axis 40 on first clamping part 34, specifically, at the location of counter bore 46. Preferably, first clamping part 34 of patella clamp 30 may include fixation pegs or spike 48 to dig into the articular surface of patella 12 so as to limit the movement of the patella during a subsequent drilling step.

Further, second clamping part 36 of patella clamp 30 may be placed on the anterior skin of the knee with a recess 50 surrounding patella 12. Recess 50 of modular clamping part 36 is placed over the anterior midline incision and drill guide 38 located at the center of recess 50 along axis 42 so that the axis 40, 42 and 44 are all coaxial. Drill guide 38 is first used to accommodate a drill bit used to create a hole or pathway through patella 12 from anterior surface 24 and exiting the articular surface 26. Drill guide 38 includes an upper stop surface 39 surrounding opening 52. Drill guide 38 may be later used to accommodate a drive shaft used to connect to a reamer device for resecting articular surface 26 of patella 12 and preparing the patella to receive a patella component thereon.

FIG. 3 is an assembled isometric view of the clamping end of patella clamp 30 of FIG. 2 engaging the patella of FIG. 1. Drill guide 38 is attached to patella clamp 30, which is used to center drill hole 52 on patella 12. The central axis of drill guide 44 is axially aligned with axis 40, 42 of the first and second clamping parts. Preferably, the patella clamp 30 extends medially or laterally and is set perpendicular to the patellar tendon. The preferred patella clamp is secured into place by squeezing handles 54 shown in FIG. 2.

Figure 4:
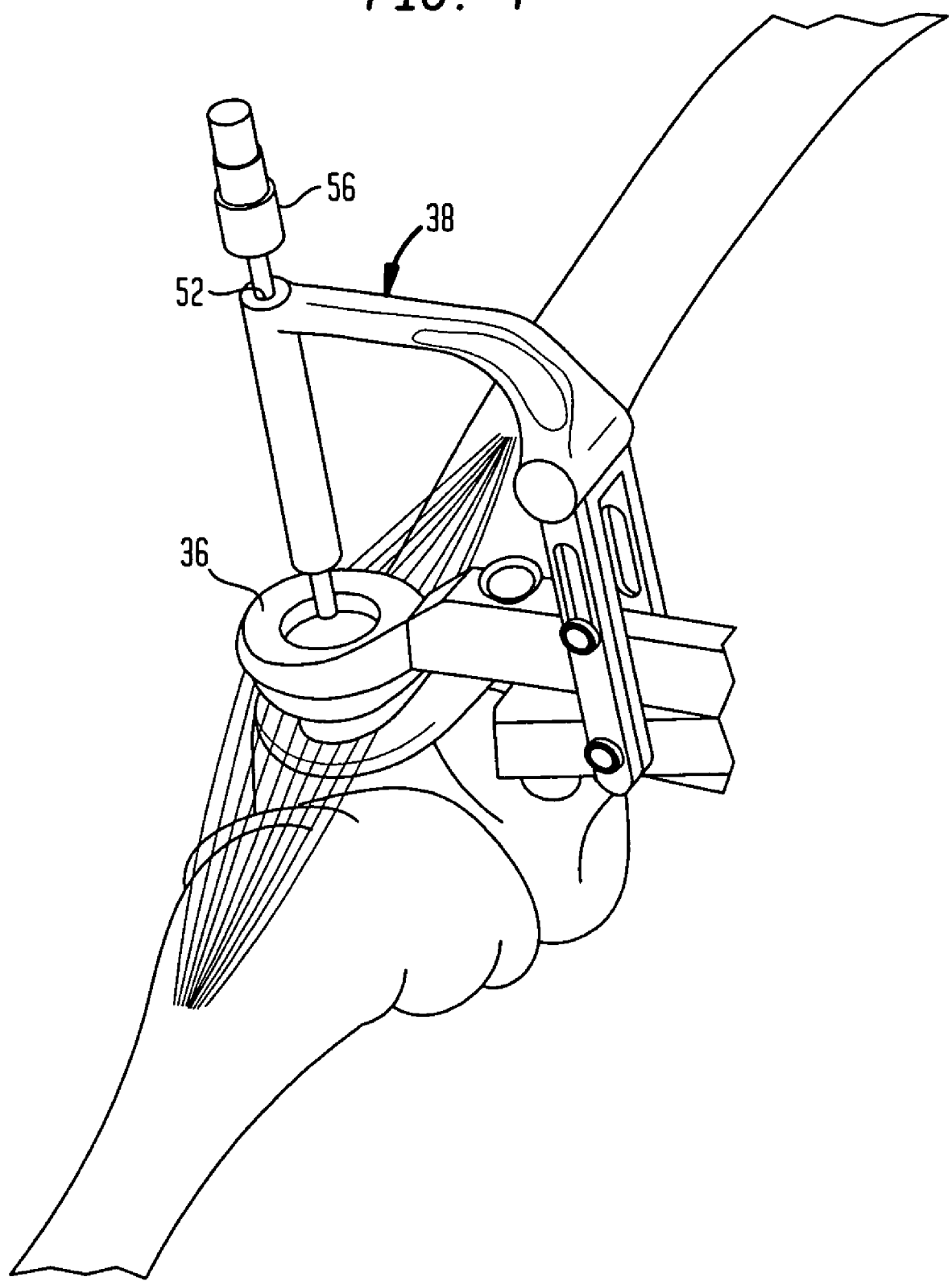
FIG. 4 is an isometric view of a drill bit inserted into the drill guide attached to the patella clamp of FIG. 2 and into the patella of FIG. 1.

FIG. 4 is an isometric view of the clamping end of patella clamp 30 with a drill bit 56 inserted into an aperture 52 the drill guide 38 attached to patella clamp 30 of FIG. 2. After passing through drill guide 38, drill bit 56 may be placed through a small anterior midline incision made through the anterior skin of the knee (not shown) until it touches anterior surface 24 of patella 12. Preferably, drill bit 56 is then advanced through anterior surface 24 and exiting articular surface 26 of patella 12. As shown in FIG. 2, the first clamping part 34 of the patella clamp 30 preferably includes a counter bore or hole 46 to allow drill bit 56 to extend outwardly beyond articular surface 26 of patella 12. By lifting the patella 12 the end of the drill bit will be spaced from the trochlear groove area and this will protect the anterior aspect of the native femur.

Figure 5:
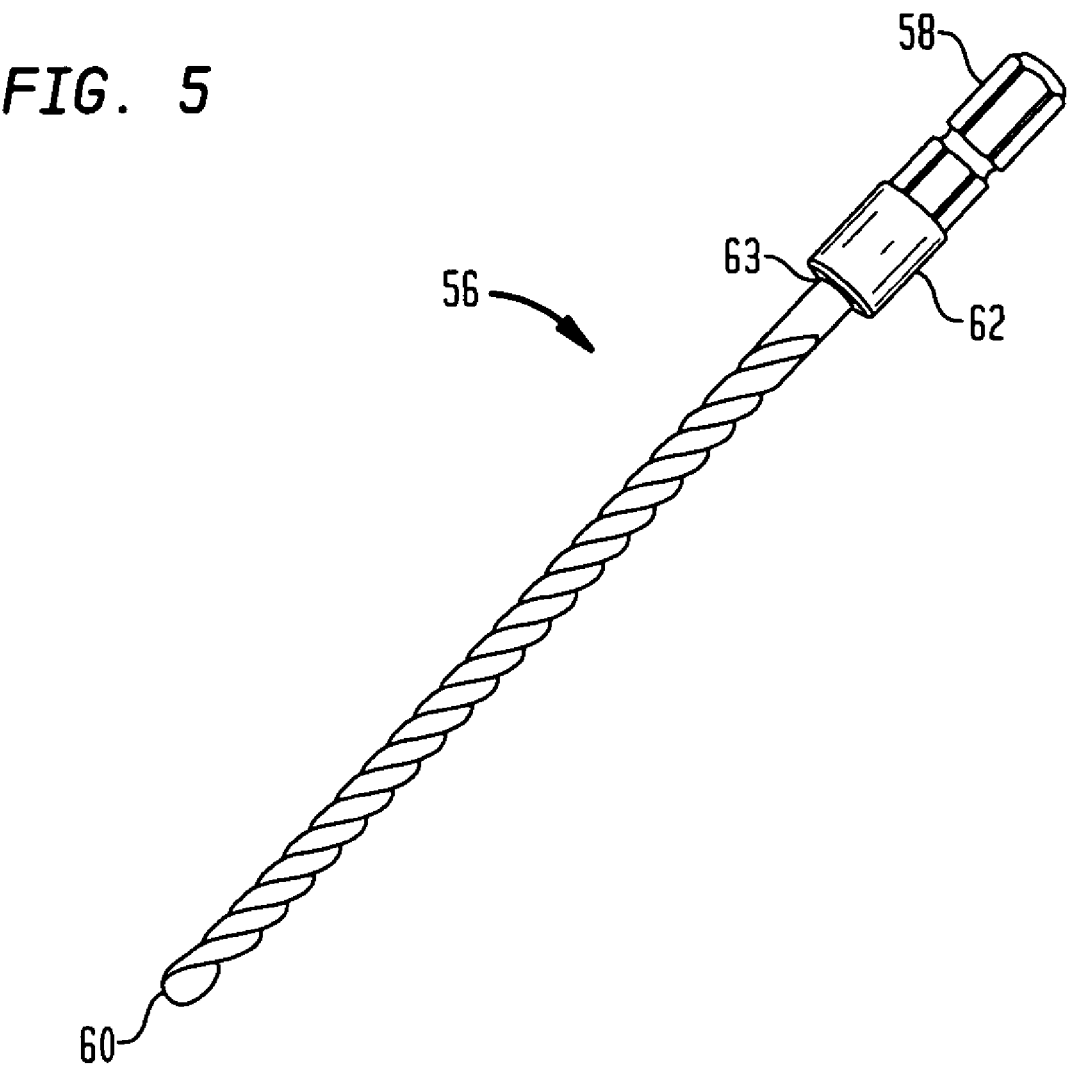
FIG. 5 is an isometric view of the drill bit of FIG. 4.
Figure 6:
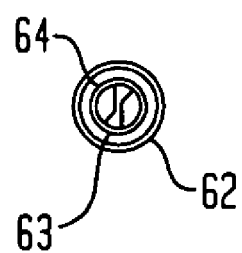
FIG. 6 is a bottom view of the drill bit of FIG. 4.

An isometric view of a preferred embodiment of a drill bit 56 is shown in FIG. 5. Drill bit 56 includes a top portion 58 which is configured to be inserted into a driver mechanism, such as a power tool that will rotate a cutting surface 60 of drill bit 56 and thus remove bone from patella 12. It will be understood and appreciated by those skilled in the art that the structure of the drill bit, including top portion 58 and cutting surface 60 of this preferred embodiment is configurable in any one of a number of designs to create the desired result of drilling through bone, specifically patella 12. Preferably, drill bit 56 further includes a stopping portion 62, which has a stop surface 63 configured to engage surface 39 and prohibit the drill bit 56 from advancing any further through the aperture 52 of drill guide 38 once the stop surface 63 of stopping portion 62 comes in contact with top portion 39 of drill guide 38. FIG. 6 is a bottom view of the drill bit 56 with a larger diameter representing the outer diameter of stopping portion 62, and a smaller diameter 64 representing the diameter of cutting surface 60 of drill bit 56 with stop surface 63 extending therebetween.

Figure 7:
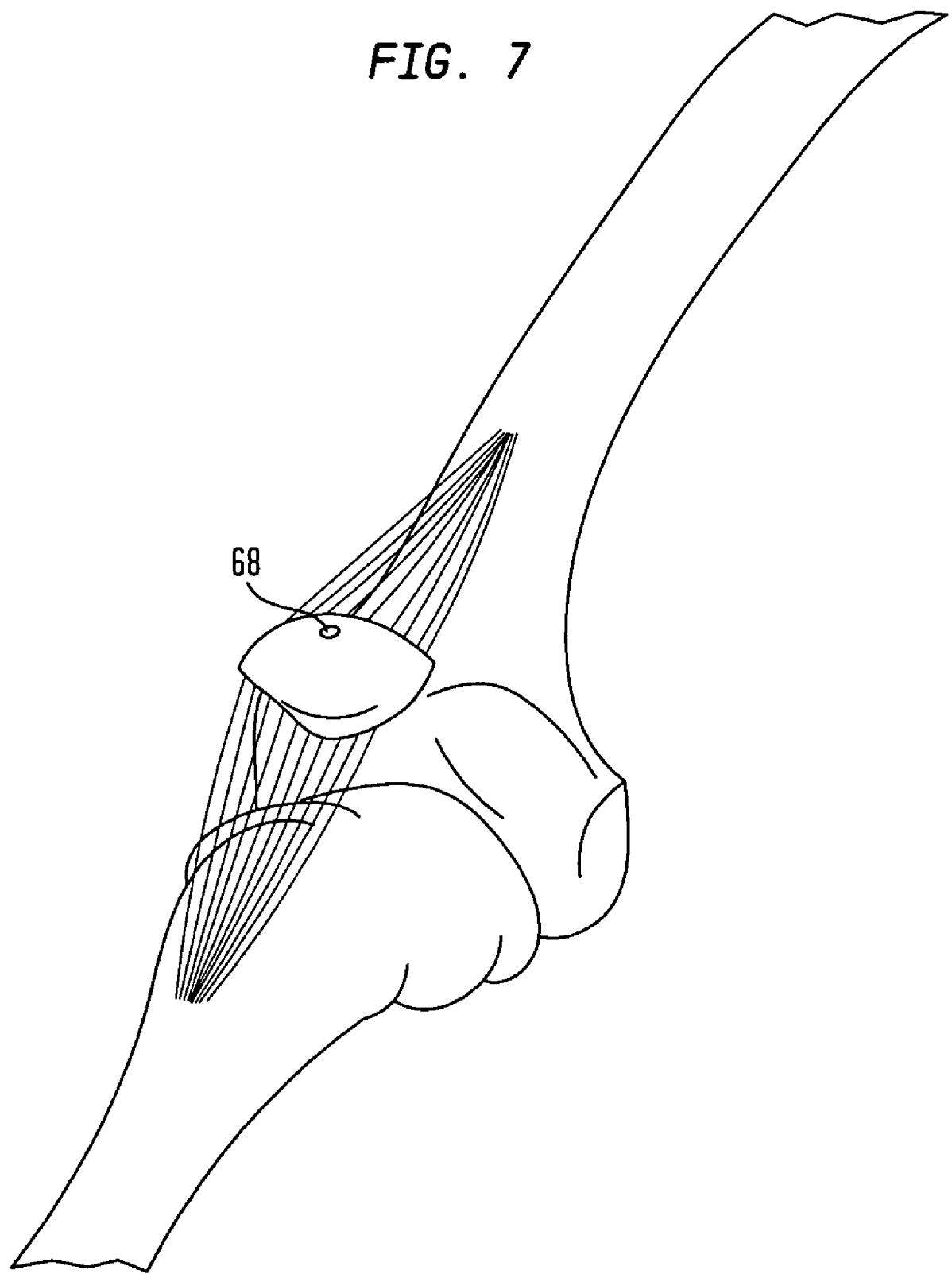
FIG. 7 is an isometric view of the resulting hole in the patella of FIG. 1 after the patellar clamp of FIG. 2 and drill bit of FIG. 4 are removed from the patella.

FIG. 7 is an isometric view of the knee joint with the drilled hole 68 in patella 12 after patellar clamp 30 and drill bit 56 are removed from patella 12 upon completion of the drilling step. The resulting hole 68 has approximately the same to slightly larger diameter as smaller diameter 64 representing the diameter of cutting surface 60 of drill bit 56. Preferably, this hole 68 is able to accommodate a drive shaft therethrough which will attach to a reamer device and be able to ream articular surface 26 of patella 12 as described below.

Figure 13:
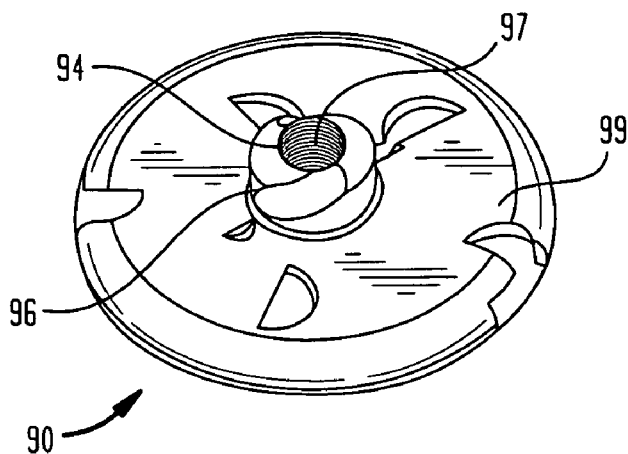
FIG. 13 is an isometric view of a reaming device to be coupled to the drive shaft of FIG. 9.
Figure 14:
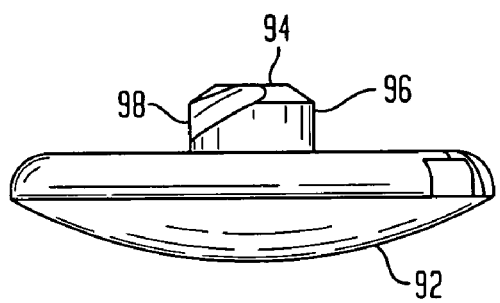
FIG. 14 is a side view of the reaming device of FIG. 13.
Figure 15:
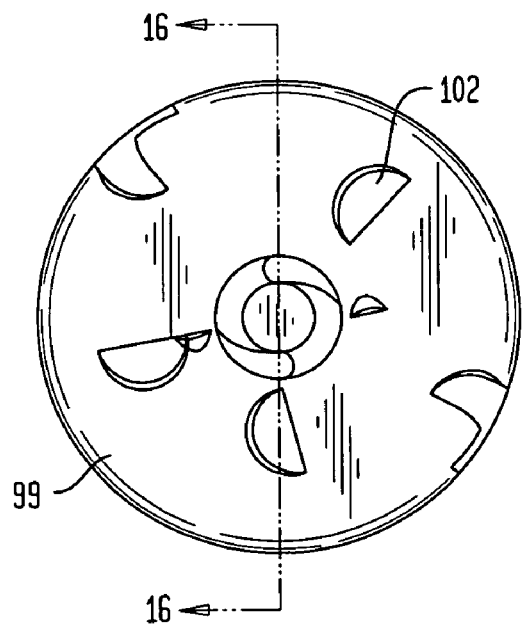
FIG. 15 is a top view of the reaming device of FIG. 13 showing the cutting surface.
Figure 16:
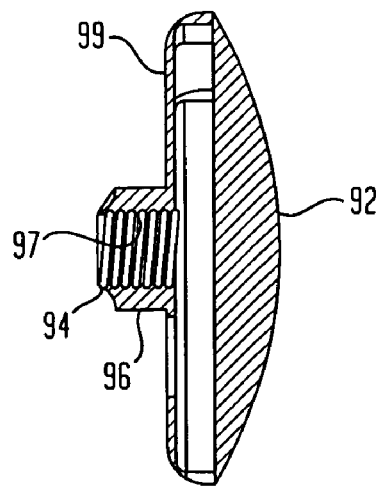
FIG. 16 is a cross sectional view taken along line 16-16 of FIG. 15.

FIG. 8 is an isometric view of a reamer drive 70 inserted into and through hole 68. FIGS. 9-11 depict a preferred embodiment of a reamer drive 70 as shown in FIG. 8. Referring to FIGS. 8-11 drive shaft 71 includes an upper drive portion 72 which is configured to be inserted into a driver mechanism, such as a power tool used to rotate a drive shaft 71. Drive shaft 71 has a threaded portion 74 which mates with a threaded receiving portion of a reamer. It will be obvious to an ordinary person skilled in the art to have drive shaft 71 include any of a various different connection portions such as a quick connect portion that can couple the end of drive shaft 71 with a receiving end 96 of a reamer 90 shown in FIG. 13, such as but not limited to threads tapers, press-fit and spring detent mechanisms. Drive shaft 71 further includes a stopping portion 76, which is configured to prohibit the reamer drive 70 from advancing any further through aperture 52 of drill guide 38 once a stop surface 78 of stopping portion 76 comes in contact with top portion 39 of drill guide 38. FIG. 10 is a bottom view of the reamer drive 70 with a larger diameter 80 representing the outer diameter of stopping portion 76, and a diameter 82 representing the diameter of the shaft 71 and diameter 83 representing the diameter of thread 74 which is the preferred embodiment of a connection feature. Surface 78 is formed between diameters 76 and 82. Referring to FIG. 11, depth gauge markings 84 are provided along at least part of the length of drive shaft 71. In the preferred embodiment, once end portion 74 of drive shaft 71 is connected to a thread bore 97 of receiving portion 96 of reamer 90, these depth gauge markings 84 can be used for measuring the depth of the cut in articular surface 26 of patella 12.

The depth of the cut can be determined several ways. In a preferred embodiment, a depth gauge may be placed through the patella 12 with a surgeon placing its end flush with articular surface 26 of patella 12 to assess its overall thickness and using the depth gauge markings 84 on drive shaft 71 to remove the desired amount of bone from articular surface 26. In an alternate embodiment, a cannula 86 having a bore 89 as shown in FIG. 12, may be placed through drilled hole 68 previously made in the patella 12. The cannula 86 has depth gauge markings 88 on the outside surface which may be used to help set the depth of the resection. Drive shaft 71 is then inserted into 89 of cannula 86 and connected to receiving end of reamer device 40 shown in FIGS. 13-16 as previously described, through any one of a number of quick connect features. Once reamer head 90 begins to rotate and is pulled anteriorly, a top surface 94 of reamer 90 will touch the cannula 86 and set the depth limit. The cannula bore 89 has a diameter that is slightly larger than diameter 82 of drive shaft 71.

Referring to FIGS. 13-16, there is shown a preferred embodiment of reaming device 90. To assemble reaming device 90 to drive shaft 71 in situ, reamer device 90 is inserted through a medial or lateral parapatellar incision made through the skin of the knee. Preferably, the posterior facing surface 92 of reamer device 90 is made of a non-abrasive material such as polyethylene so as to minimize any damage on the anterior femur during reaming. Preferably, reamer device 90 is available in several diameters to approximate a range of sizes of patella 12.

Figure 17:
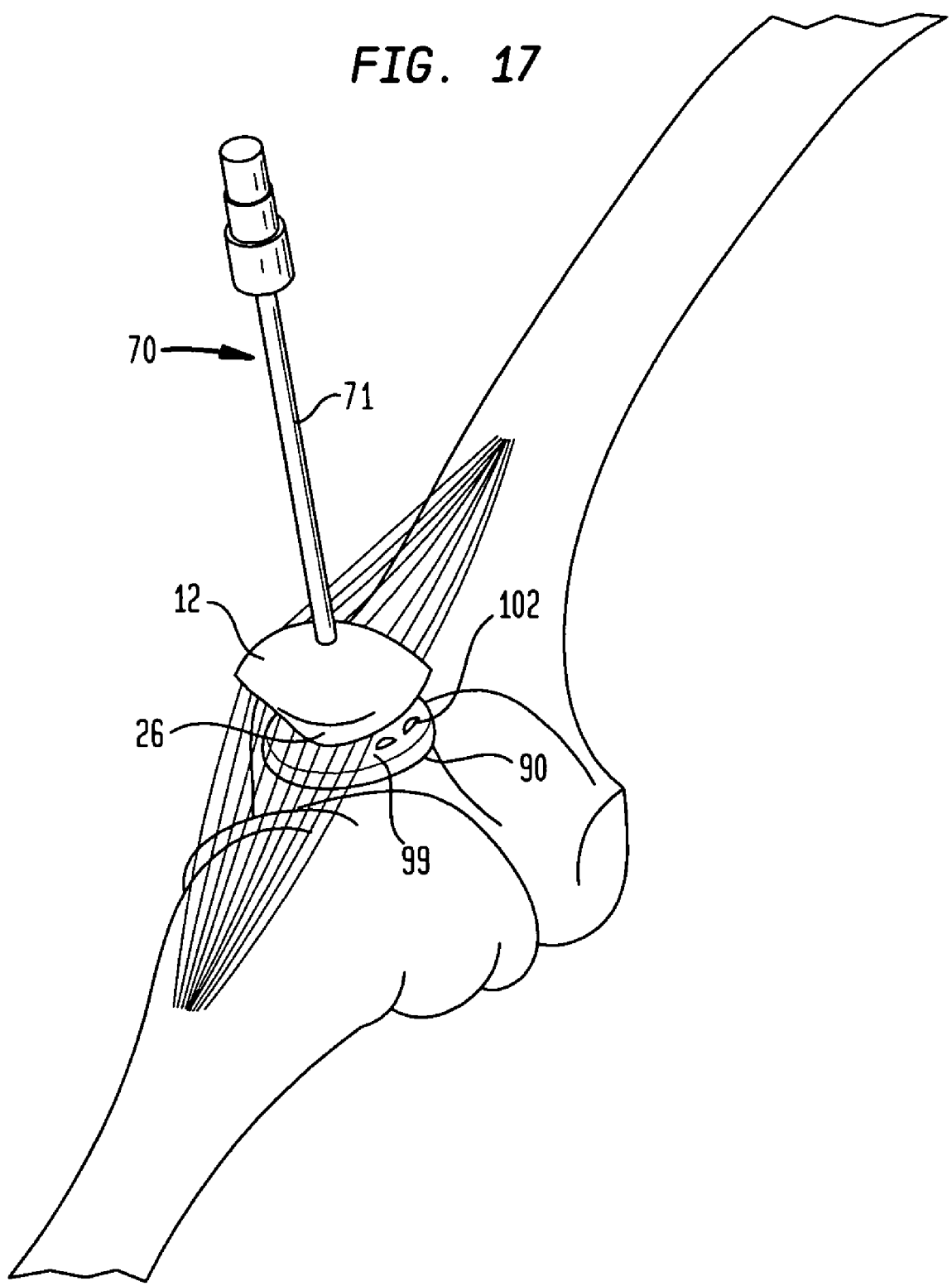
FIG. 17 is an isometric view of a reaming device in contact with the articular surface of the patella of FIG. 1 with the reaming device connected to the drive shaft of FIG. 9.
Figure 18:
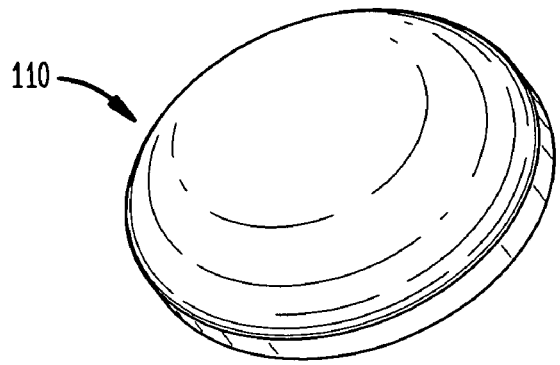
FIG. 18 is an isometric view of a patellar component to be used after the patella is prepared by the reamer of FIG. 13.
Figure 19:
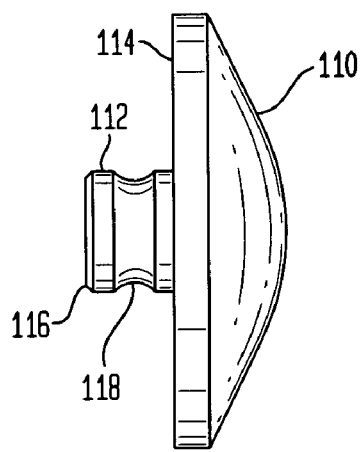
FIG. 19 is a side view of the patellar component of FIG. 18.
Figure 20:
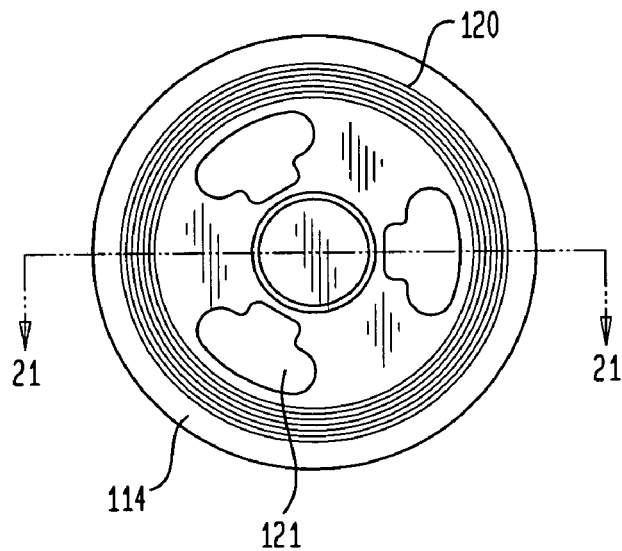
FIG. 20 is a bottom view of the patellar component of FIG. 18 showing the bone contacting surface.
Figure 21:
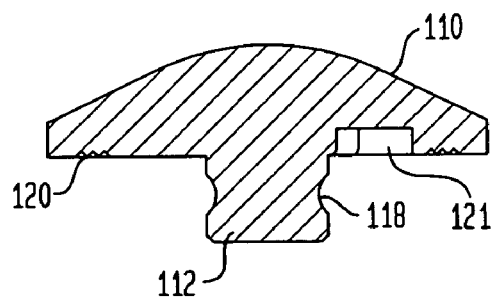
FIG. 21 is a cross sectional view taken along line 21-21 of FIG. 20.

A quick connect feature is provided to couple reamer 90 to shaft 71. In the preferred embodiment threaded end 74 of drive shaft 71 is configured to mate with threaded bore 97 of receiving end 96 of a reamer device 90. After the two threaded elements are joined the anterior surface 94 of the receiving end is placed in contact with articular surface 26 of patella. Top surface 94 of receiving end 96 forms a starting point for a bore cutting surface 98, which on anterior movement, creates a cylindrical recess 13 (shown in FIG. 23) in patella 12 as the reamer device is rotated during the reaming step. Reamer device further includes cutting teeth 102 in cutting surface 99. When pressure is applied between articular surface 26 of patella 12 and surface 94 of receiving end 96 of reamer device 90 while pulling a rotating drive shaft anteriorly and preferably applying downward force on the anterior surface 24 of the patella, cartilage and then bone will begin to be removed from the articular surface 26 of patella 12 and receiving end 96 will create the cylindrical recess 13 in patella 12. Eventually, cutting teeth 102 of reamer device 90 will begin to remove cartilage and bone from articular surface 26 of patella and create a flat, stable platform to mate with a flat anterior surface of a prosthetic patellar component. Preferably, a desired amount of bone may be removed through use of the depth gauge markings 84 of drive shaft 71 or cannula 86. FIG. 17 illustrates reaming device 90 in contact with articular surface 26 of patella 12. The reaming device is shown connected to drive shaft 71.

After the reaming step takes place, the reamer device 90 may be disassembled from end 74 of drive shaft 71. Preferably, the drive shaft 71 is removed back through the anterior midline incision in the skin of the knee. The reamer device 90 may be removed back through the medial or lateral parapatellar incision. Next, a patellar component 110 illustrated in FIGS. 18-21, is inserted through the medial or lateral parapatellar incision. In the preferred embodiment patellar component 110 may include a central peg 112 that protrudes from top surface 114. The central peg 112 mates with recess 13 of patella 12 created during the reaming step. The central peg includes a chamfer portion 116 which may be in the form of a taper for easy insertion of central peg 112 into recess 13. Additionally, central peg 112 may further include a recessed portion 118. Preferably, the anterior surface 114 of the patellar component 110 further includes a plurality of grooves 120 which create friction between the prepared resected surface 15 of the patella and the anterior facing surface 114 of the patella component 110 that creates a stabilizing fit between the two mated surfaces. Surface 114 of the patella may contain recesses 121 which may receive bone cement on cementing the patellar component to the prepared bone.

Figure 22:
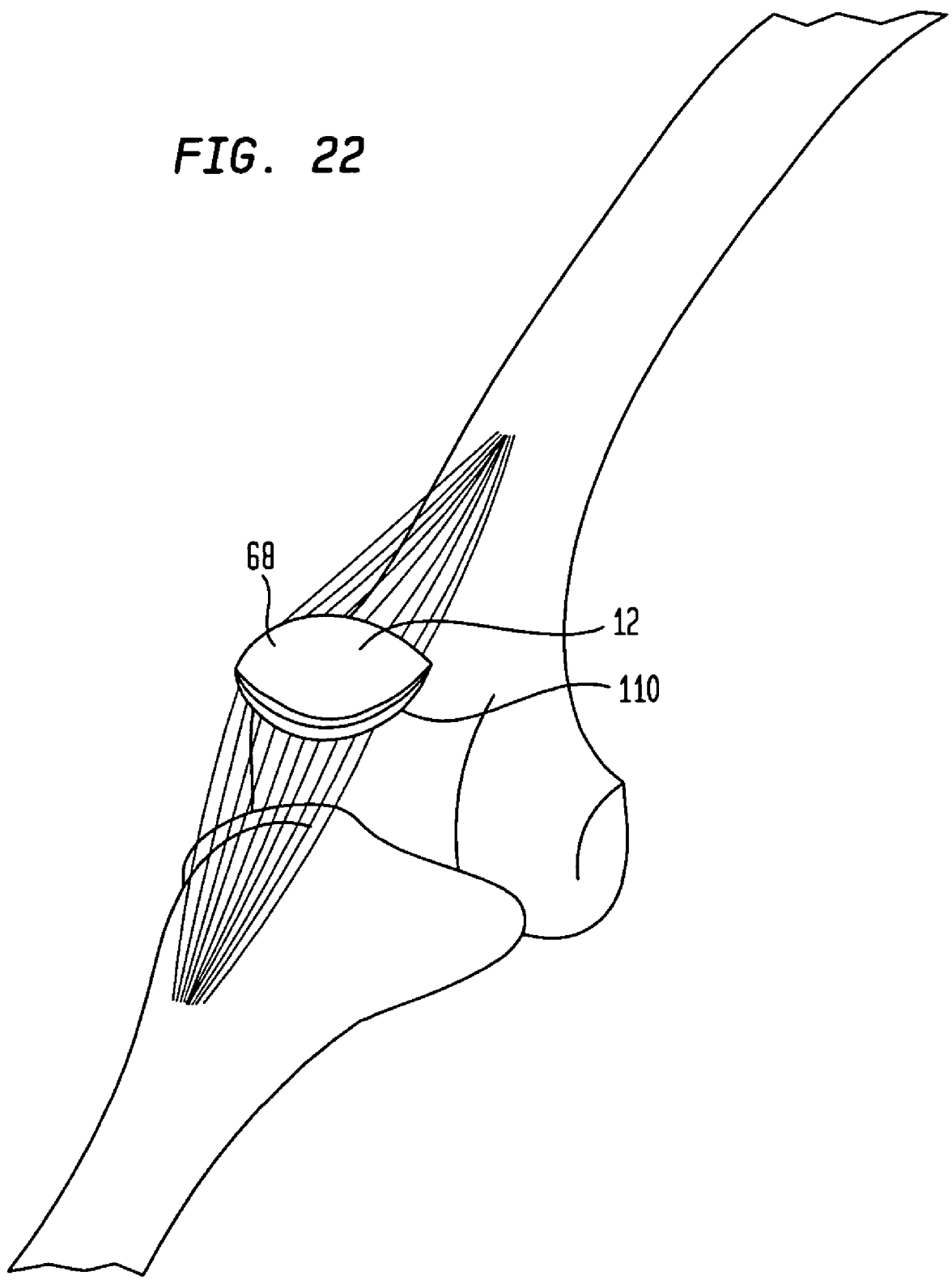
FIG. 22 is an isometric view similar to FIG. 1 showing patellar component of FIG. 18 with the patella.
Figure 23:
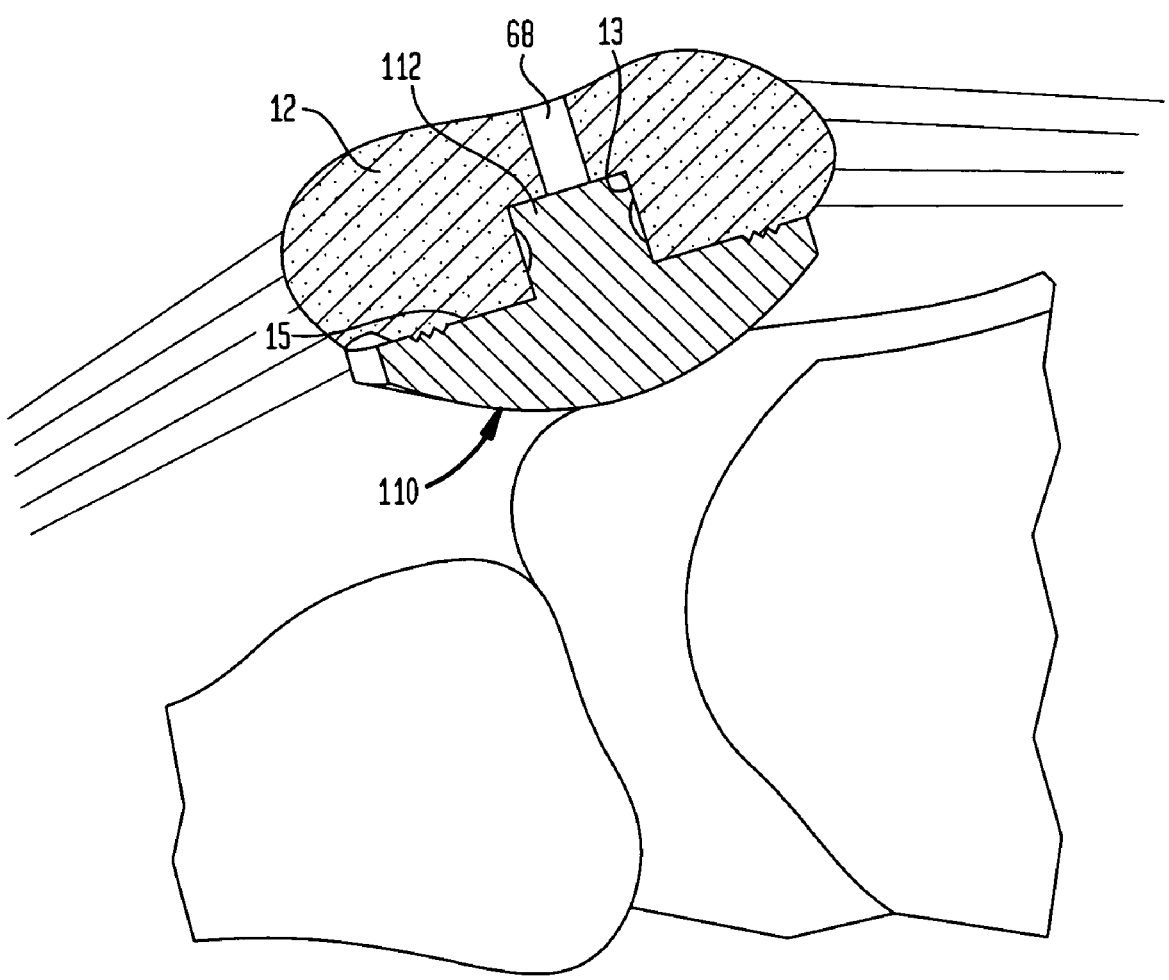
FIG. 23 is an isometric cross-sectional view of a patellar component connected to the articular surface of the patella of FIG. 1 along lines 23-23 of FIG. 22.

FIG. 22 is alternate view of the assembled patellar component 110 and patella 12. FIG. 23 is a view of the central peg 112 of the patellar component 110 mated with recess 13 of patella 12. The mated resected surface 15 of patella 12 and top surface 114 of patellar component 110 is also illustrated. After the patellar component 110 is cemented into place, any skin incision previously made in the knee may be closed.

Figure 24:
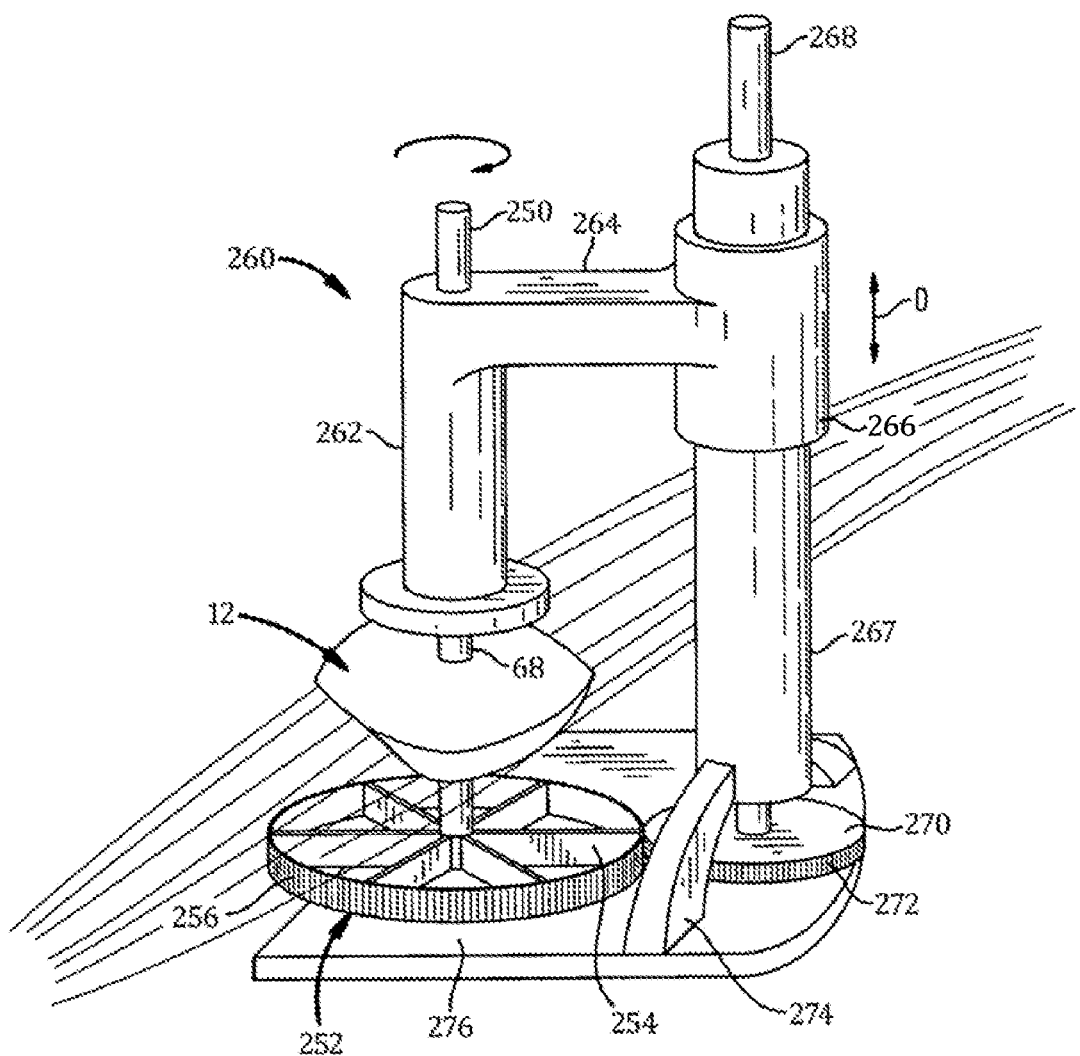
FIG. 24 shows an alternate embodiment of the patella reaming system of the present invention wherein a drive is radially offset from the patella reamer.

Referring to FIG. 24 there is shown a patella 12 utilizing a guide pin 250 extending through bore 68 integrally connected to the reamer 252 having anteriorly facing cutting surfaces or teeth 254. Reamer 252 includes a plurality of gear teeth 256 around the outer circumference thereof. Guide pin 250 and reamer 252 are supported in a jig generally noted as 260 which has a cylindrical bushing 262 housing guide pin 250. Bushing 262 is connected by arm 264 to a second bushing 266 which houses slidable housing 267. Housing 267 in turn receives drive shaft 268 which is connected to a drive gear 270. It can be seen as gear 270 rotates teeth 272 thereon engage teeth 256 of reamer 252 to transfer the drive forces from drive shaft 268 to reamer 252.

In this embodiment slidable housing 267 is connected via a pair of arms 274 to a base 276. If desired drive pin 250 and drive shaft 268 can extend through base plate 278 with the tip of drive shaft 268 being flush with the posteriorly facing surface of plate 278. Housing 267 can slide within second bushing 267 such that the cutting teeth 254 of reamer 252 engage the posterior surface of the patella as housing 267 is moved anteriorly in direction D to prepare the surface of the patella. The advantage of using an offset drive system as shown in FIG. 24 is that greater torque can be transmitted into reamer 252 by a gear drive system than can be transmitted by a small diameter drive shaft 70.

Figure 25A:
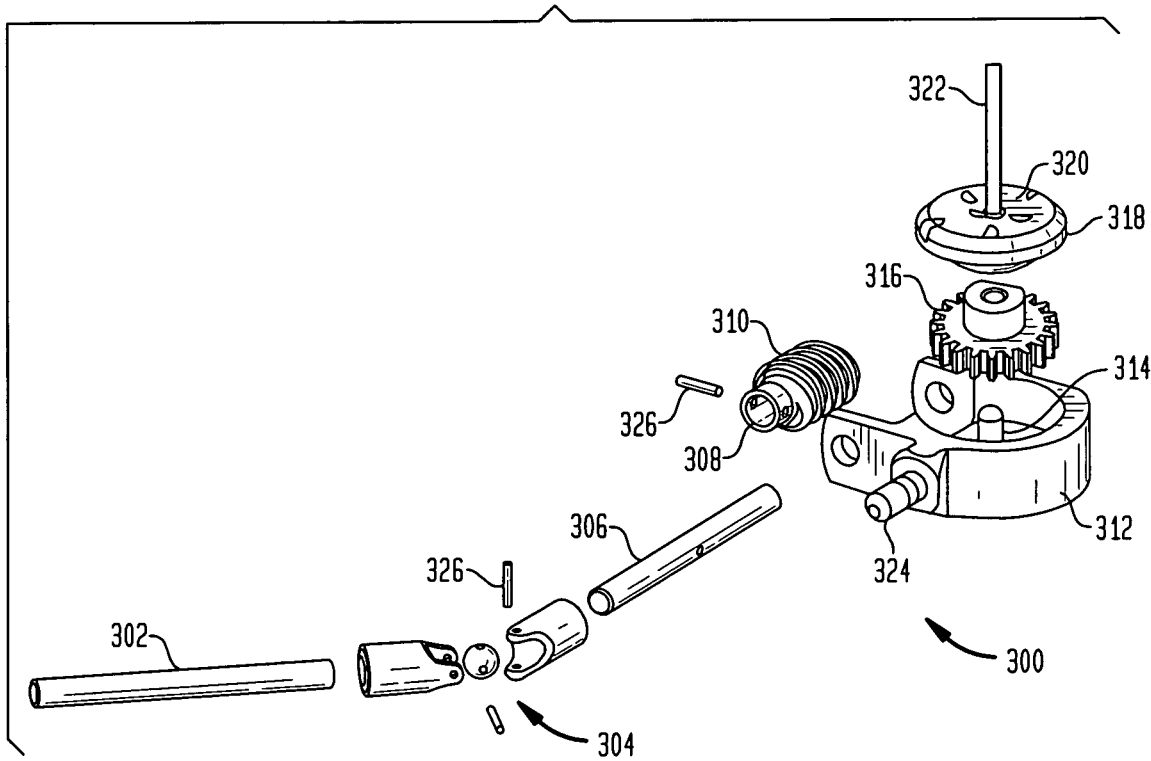
FIG. 25A shows an exploded view of an additional embodiment of the present invention.

Referring to FIG. 25A there is shown an exploded view of an additional embodiment which is generally denoted as 300. The embodiment 300 includes a drive shaft 302 coupled to a ball joint generally denoted as 304 coupled to a worm gear shaft 306. Worm gear shaft extends through an opening 308 of worm gear 310 which fits inside housing 312. Housing 312 includes an axle 314 in which a drive pinion 316 is mounted. Drive pinion 316 is operatively connected to reamer 318 which has a face 320 for engaging the posterior surface of the patella. The guide shaft 322 extends through the patella (not shown) as do the guide and drive shafts previously described, for example shaft 70. An attachment element 324 is fixed to housing 312 so that the reaming system 300 may be attached to the clamping handle of FIG. 2. The U-joints and drive shaft are coupled to the respective gear and U-joint portions by typical pins 326 for the transmission of the drive torque.

Figure 25B:
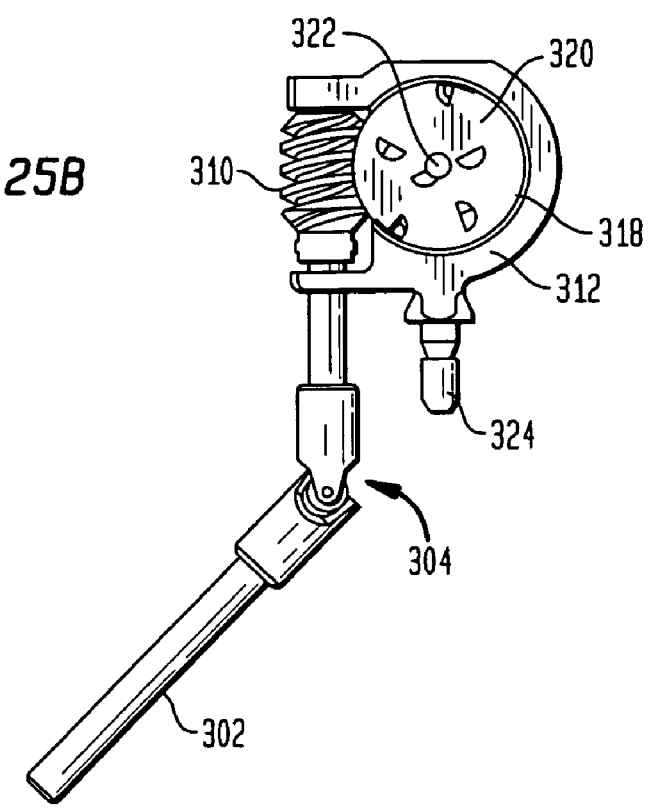
FIG. 25B shows a top view of this alternate embodiment of the present invention in an assembled condition.
Figure 25C:
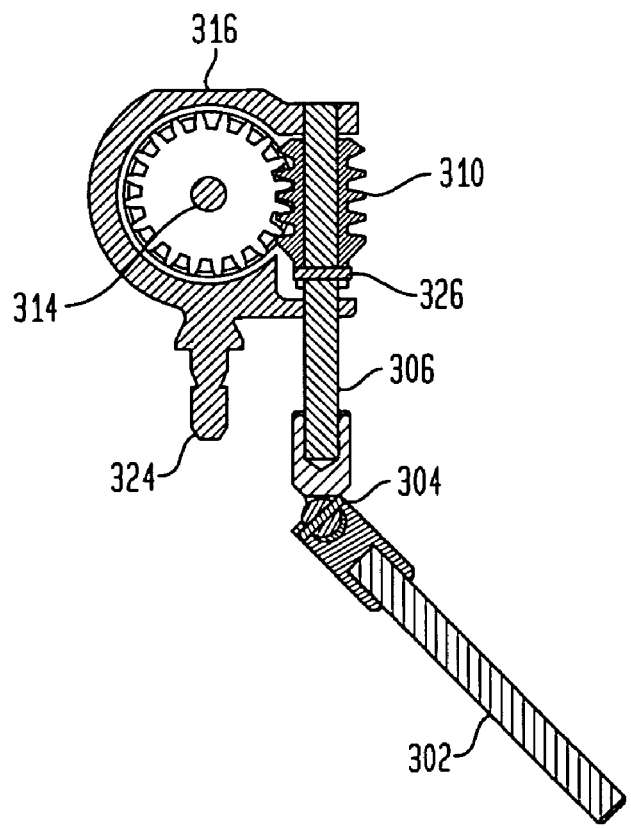
FIG. 25C shows a cross-sectional view of the additional embodiment through the plane of the page.

Referring to FIGS. 25B and 25C there is shown a top and cross-sectional view respectively, of the alternate reaming system of FIG. 25A. In FIG. 25B the system 300 is assembled showing the drive shaft 302 driving the worm gear 310 via U-joint 304. This in turn drives cutting face 320 of reamer 318 which is rotatably mounted in housing 312. The coupling element 324 is shown in both FIGS. 25B and 25C. Referring to FIG. 25C pinion gear 316 is shown being driven by worm gear 310 via shaft 302, U-joint 304 and worm gear shaft 306 which is now coupled to the worm gear via pin 326.

Figure 26A:
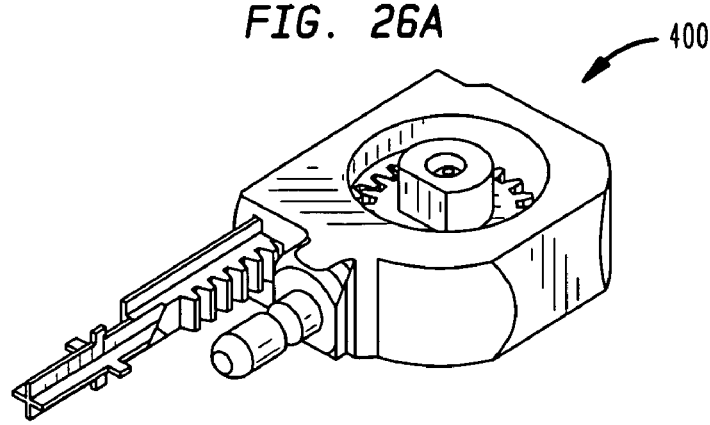
FIG. 26A shows an assembled view of yet a further embodiment of the present invention.
Figure 26B:
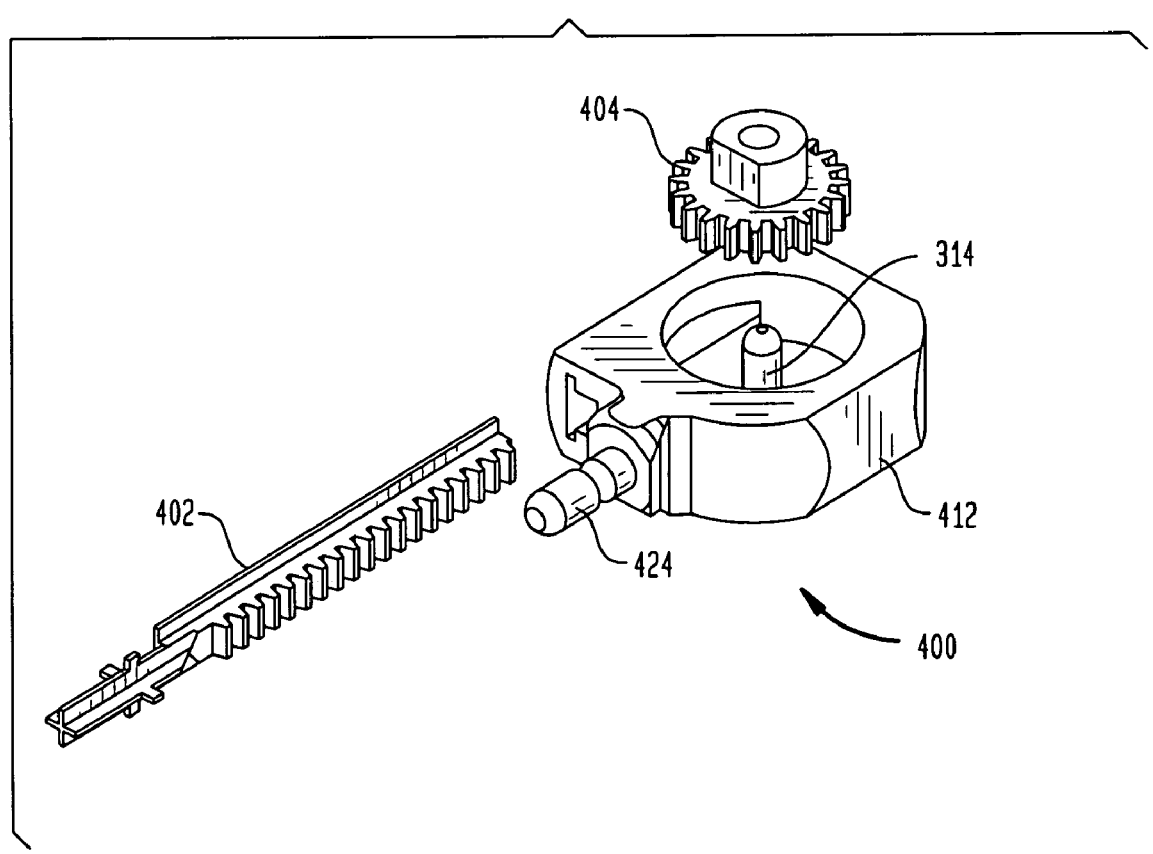
FIG. 26B shows an exploded view of the further embodiment of FIG. 26A.

Referring to FIGS. 26A and 26B there is shown yet a further alternate embodiment generally denoted as 400 which is in the form of a rack and pinion system. Embodiment 400 includes rack 402 and pinion 404 again mounted in a housing 412 including an axle 314 to which pinion 404 is fixedly attached. Again housing 412 includes attachment coupling element 424 for coupling the drive system 400 to the handle of FIG. 2. Although the reamer is not shown in FIGS. 26 and 26B it is fixedly coupled to pinion 404 for rotation therewith. Obviously a drive system would be used to reciprocating rack 402 which in turn would rotate pinion 404 first in one direction and then in the other direction which in turn drives the reamer which resects the posterior surface of the patella as described hereinbefore.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of preparing the articular surface of a patella to receive a patellar component comprising:
    making at least one incision in the skin of the knee;
    placing a drill on the anterior surface of the patella and drilling a hole from the anterior surface of the patella through the posterior articular surface of the patella;
    inserting a drive shaft through the drilled hole of the patella, the drive shaft having a first end that extends outwardly beyond the articular surface;
    attaching the first end of the drive shaft to a receiving end of a reamer device;
    placing the reamer device in contact with the articular surface of the patella;
    resecting the articular surface of the patella by rotating the reamer device and moving the drive shaft anteriorly such that the reamer device removes bone from the articular surface of the patella; and
    inserting a patellar component through the at least one incision and securing the patellar component to the resected articular surface of the patella.

2. The method according to claim 1 further including providing a patella clamp having a first clamping part and a second clamping part for respectively engaging the anterior and posterior surfaces of the patella, the clamp including a drill guide; and disengaging the first and second clamping parts from the patella after drilling the hole from the anterior surface of the patella through the articular surface of the patella.

3. The method according to claim 1 wherein the reamer device has a bore forming element configured to prepare a recess in the articular surface of the patella as the drive shaft is rotated and moved anteriorly.

4. The method according to claim 3 wherein the patellar component includes a central peg for engaging said recess.

5. A method of implanting a prosthetic patellar component comprising:
    making a parapatellar incision through the skin of the knee;
    drilling a hole from the anterior surface of the patella through the articular surface of the patella;
    inserting a drive shaft through the drilled hole of the patella, the drive shaft having a first end that extends outwardly beyond the articular surface;

inserting a reamer device having a coupling end through the parapatellar incision;

coupling the first end of the drive shaft to the coupling end of a reamer device;

resecting the articular surface of the patella by rotating the drive shaft and reamer and moving them anteriorly to prepare the articular surface of the patella; and inserting a patellar component through the parapatellar incision and securing the patellar component to the resected articular surface of the patella.

6. The method according to claim 5 wherein the first clamping part, the second clamping part, and the drill guide each have a central axis.

7. The method according to claim 6 further including the step of aligning the central axis of each of the first clamping part, the second clamping part, and the drill guide before drilling the hole from the anterior surface of the patella through the articular surface of the patella.

8. The method according to claim 5 further including providing a patella clamp having a first clamping part and a second clamping part for respectively engaging the anterior and posterior surfaces of the patella, the clamp including a drill guide; and disengaging the first and second clamping parts from the patella after drilling the hole from the anterior surface of the patella through the articular surface of the patella.

9. The method according to claim 5 further including the step of centering the reamer device on the articular surface of the patella.

10. The method according to claim 5 wherein said reamer device includes a plurality of anteriorly facing cutting sites.

11. A method of preparing the posterior surface of a patella to receive a patellar component comprising:

making at least two incisions in the skin of the knee;

placing a drill through a first of the at least two incisions and onto an anterior surface of the patella;

drilling a hole with the drill from the anterior surface of the patella through the posterior surface of the patella along a central axis;

inserting a guide shaft through the drilled hole, the guide shaft having a first end that extends outwardly beyond the posterior surface of the patella;

inserting a reamer having a drive shaft attached thereto through the second of the at least two incisions along an axis transverse to the central axis;

attaching the first end of the guide shaft to a receiving end of the reamer;

placing a cutting surface of the reamer in contact with the posterior surface of the patella; and resecting the posterior surface of the patella by rotating the reamer by way of the drive shaft and moving the reamer anteriorly such that the reamer removes bone from the posterior surface of the patella.

12. The method according to claim 11, further comprising:

providing a patella clamp having a first clamping part and a second clamping part for respectively engaging the anterior and posterior surface of the patella, the clamp including a drill guide to guide the drill along the central axis.

13. The method according to claim 12, further comprising:

disengaging the first and second clamping parts from the patella after drilling the hole from the anterior surface of the patella through the posterior surface of the patella.

14. The method according to claim 12, wherein the first clamping part, the second clamping part, and the drill guide each have a central axis.

15. The method according to claim 14, further comprising aligning the central axis of each of the first clamping part, the second clamping part, and the drill guide before drilling the hole from the anterior surface of the patella through the posterior surface of the patella along the central axis.

16. The method according to claim 11, wherein the reamer has a bore forming element configured to prepare a recess in the posterior surface of the patella as the drive shaft is rotated and the reamer is moved anteriorly.

17. The method according to claim 16, wherein the patellar component includes a central peg for engaging the recess.

18. The method according to claim 17, further comprising:

inserting the patellar component through the second of the at least two incisions; and securing the patellar component to the resected posterior surface of the patella by aligning the central peg of the patellar component with the prepared recess of the posterior surface of the patella.

* * * * *

UNITED STATES PATENT AND TRADEMARK OFFICE
CERTIFICATE OF CORRECTION

PATENT NO. : 7,758,651 B2  Page 1 of 1
APPLICATION NO. : 11/583469
DATED : July 20, 2010
INVENTOR(S) : Sandeep K. Chauhan et al.

It is certified that error appears in the above-identified patent and that said Letters Patent is hereby corrected as shown below:

On the Title Pg, Item (75) Inventors, please delete the current text and replace with the following:

--Sandeep K. Chauhan, Plumpton Green (GB)--

Signed and Sealed this

Seventh Day of September, 2010

David J. Kappos
*Director of the United States Patent and Trademark Office*